(12) United States Patent
Niazi et al.

(10) Patent No.: US 9,884,087 B1
(45) Date of Patent: Feb. 6, 2018

(54) COMPOSITIONS AND METHODS OF IMPROVED WOUND HEALING

(71) Applicant: Chan Soon-Shiong Institute of Advanced Health, Culver City, CA (US)

(72) Inventors: Kayvan Niazi, Los Angeles, CA (US); Shahrooz Rabizadeh, Los Angeles, CA (US); Justin Golovato, Los Angeles, CA (US); Oleksandr Buzko, Los Angeles, CA (US); Anne-Laure LeNy, South Pasadena, CA (US); Patrick Soon-Shiong, Los Angeles, CA (US)

(73) Assignee: CHAN SOON-SHIONG NANTHEALTH FOUNDATION, Culver City, CA (US)

( * ) Notice: Subject to any disclaimer, the term of this patent is extended or adjusted under 35 U.S.C. 154(b) by 2 days.

(21) Appl. No.: 14/270,193

(22) Filed: May 5, 2014

Related U.S. Application Data

(60) Provisional application No. 61/819,413, filed on May 3, 2013.

(51) Int. Cl.
| | | |
|---|---|---|
| *A61K 38/00* | (2006.01) | |
| *A61K 38/17* | (2006.01) | |
| *A61K 31/341* | (2006.01) | |
| *A61K 31/407* | (2006.01) | |
| *A61K 31/05* | (2006.01) | |
| *A61K 31/365* | (2006.01) | |
| *A61K 31/702* | (2006.01) | |

(52) U.S. Cl.
CPC .......... *A61K 38/1709* (2013.01); *A61K 31/05* (2013.01); *A61K 31/341* (2013.01); *A61K 31/365* (2013.01); *A61K 31/407* (2013.01); *A61K 31/702* (2013.01)

(58) Field of Classification Search
None
See application file for complete search history.

(56) References Cited

U.S. PATENT DOCUMENTS

| | | |
|---|---|---|
| 8,247,227 B2 | 8/2012 | Cohen et al. |
| 2005/0070506 A1 | 3/2005 | Doherty et al. |
| 2010/0272700 A1 | 10/2010 | Cohen et al. |
| 2013/0183343 A1 | 7/2013 | Czerniecki et al. |
| 2014/0037700 A1 | 2/2014 | Fisher |
| 2015/0104482 A1* | 4/2015 | Klinman ............... A61K 38/12 424/278.1 |

FOREIGN PATENT DOCUMENTS

| | | |
|---|---|---|
| WO | 2008121385 A2 | 10/2008 |
| WO | 2011115970 A1 | 9/2011 |
| WO | 2012174591 A1 | 12/2012 |

OTHER PUBLICATIONS

Mekahli et al. "Endoplasmic-Reticulum Calcium Depletion and Disease" Cold Spring Harbor Perspectives in Biology 2011;3:a004317.*

Yu et al. "Endogenous toll-like receptor ligands and their biological significance" J. Cell. Mol. Med. 14:2592-2603. Published 2010.*

Zhu et al. "Toll-like receptor ligands synergize through distinct dendritic cell pathways to induce T cell responses: Implications for vaccines" Proc. Nat. Acad. Sci. 105:16260-16265. Published Oct. 21, 2008.*

Matsushima K and Oppenheim JJ "Calcium ionophore (A23187) increases interleukin 1 (IL-1) production by human peripheral blood monocytes and interacts synergistically with IL-1 to augment concanavalin A stimulated thymocyte proliferation" Cell. Immunol. 90:226-233. Published Jan. 1985.*

Lyudmila A. Lyakh, "Monocytes Through Distinct Pathways That Cell-Like Differentiation in CD14 + Conditions Promote Rapid Dendritic Cell-Like Differentiation in CD14 + Monocytes Through Distinct Pathways That Activate NF-kB", J Immunol 2000; 165:3647-3655; http://www.jimmunol.org/content/165/7/3647.

Qingqi Jiang, "Toll-Like Receptor 4 (TLR4) Prior to Nuclear Physical Proximity Between CD14 and Toll-Like Receptor 4 (TLR4) Prior to Nuclear Translocation of NF- kB", J Immunol 2000; 165:3541-3544; http://www.jimmunol.org/content/165/7/3541.

Richard J. Ulevitch, "Therapeutics Targeting the Innate Immune System", Department of Immunology,The Scipps Research Institute, Feb. 24, 20006, pp. 1-10, vol. 4. www.nature.com/reviews/immunol.

Shizuro Akira, "Pathogen Recognition and Innate Immunity", Leading Edge Review, Feb. 24, 2006, pp. 783-801, www.plospathogens.org.

Jeongmin Song, "A Novel TLR4-Mediated Signaling Pathway Leading to IL-6 Responses in Human Bladder Epithelial Cells", PLoS Pathogens, Apr. 2007, pp. 0541-0552, www.plospathogens.org.

S. Rakoff-Nahoum, "Role of Toll-Like Receptors in Tissue Repair and Tumorigenisis", Biochemistry (Moscow), 2008, vol. 73, No. 5, pp. 690-698.

Haiwei Yang, "Upregulation of Toll-like receptor (TLR) expression and release of cytokines from P815 mast cells by GM-CSF", BMC Cell Biology, May 9, 2009, pp. 1-10, http://www.biomedcentral.com/1471-2121/10/37.

Tomohiko Murakami, "Critical role for calcium mobilization in activation of the NLRP3 inflammasome", PNAS Early Edition, Oct. 28, 2011, pp. 1-12, www.pnas.org/lookup/suppl/doi:10.1073/pnas.1117765109/-/DCSupplemental.

Bijay Parajuli, "GM-CSF increases LPS-induced production of proinflammatory mediators via upregulation of TLR4 and CD14 in murine microglia", JNI Journal of Neuroinflammation, 2012, pp. 1-12, http://www.jneuroinflammation.com/content/9/1/268.

* cited by examiner

*Primary Examiner* — Christina Bradley
*Assistant Examiner* — Zachary J Miknis
(74) *Attorney, Agent, or Firm* — Lucas & Mercanti, LLP

(57) ABSTRACT

Compositions and methods are contemplated for treatment of a wound, and especially a sterile or TLR/NOD ligand-poor wound in which contemporaneous administration of a $Ca^{2+}$-flux agonist (CFA) and a pattern recognition receptor (PRR) ligand improves wound healing.

12 Claims, 7 Drawing Sheets

COMPOSITIONS AND METHODS OF IMPROVED WOUND HEALING

This application claims priority to U.S. provisional application with the Ser. No. 61/819,413, which was filed 3 May 2013, and which is incorporated by reference herein.

FIELD OF THE INVENTION

The field of the invention is pharmaceutical compositions and methods, especially as they relate to compositions and treatment for improved wound healing.

BACKGROUND OF THE INVENTION

The background description includes information that may be useful in understanding the present invention. It is not an admission that any of the information provided herein is prior art or relevant to the presently claimed invention, or that any publication specifically or implicitly referenced is prior art.

Mammalian pattern recognition receptors (PRR) serve a critical role in maintaining healthy tissue homeostasis as sensors of microbial invaders and otherwise diseased/damaged cells. At the present time, mammalian PRR proteins are believed to be comprised of members of the toll-like receptors (TLR), C-type lectin receptors (CLR), NOD-like receptors (NLR), the RNA helicases belonging to the RIG-I-like receptor family (RLR), and secreted PRR including members of the blood complement proteins.

Perhaps the best studied of the group, TLR (which includes 10 different isotypes in man, 13 in mice) are membrane-bound proteins which recognize both pathogen-associated molecular patterns (PAMPs) as well as damage-associated molecular patterns (DAMPs). Some examples of PAMPs recognized by TLR are provided by the recognition of bacterial endotoxin by TLR4, di- and tri-acylated peptides by TLR2 containing protein complexes, viral double stranded RNA by TLR3, flagellin by TLR5, the nucleotide analog imiquimod recognition by TLR7, and CpG containing deoxyribonucleic acids (DNA) by TLR9. Sterile-injury produced DAMPs include the high-mobility group box-1 protein HMGB1, members of the heat shock protein family like HSP22, HSP70, HSP72, and gp96, or components of the extracellular matrix including such as biglycan, tenascin-C, versican, and oligosaccharides derived from hyaluronic acid and heparan sulfate. To date, TLR2 and TLR4 are believed to act as the main receptors for DAMPs.

However, while the role of PRR in numerous physiological processes, and particularly in processes associated with inflammation and immune activation has become increasingly studied, therapeutic and/or prophylactic use of such agents and their ligands has been elusive. Thus, there is still a need to provide improved therapeutic and prophylactic compositions related to PRR.

SUMMARY OF THE INVENTION

The inventors have discovered that healing of sterile wounds or TLR/NOD ligand-poor wounds can be improved/accelerated by activation of a PRR-associated pathway, and especially by TLR and/or NOD receptor activation that is further amplified by (co-)administration of $Ca^{2+}$-flux agonists (CFA) under a protocol that provides the PRR ligand and the CFA in an at least overlapping regime. In some aspects, the PRR ligand provides a non-saturating signal in the PRR pathway, and the CFA is provided in a synergistic quantity with respect to pathway activation.

In particularly preferred aspects, pharmaceutical compositions comprising one or both agents (e.g., CFA and PRR activator) are formulated for topical treatment of a wound or site of traumatic injury (which may or may not be sterile) to so provide a treatment modality that can be used for prophylaxis and/or treatment of a tissue injury, and particularly a surgical or traumatic injury. For example, especially preferred $Ca^{2+}$-flux agonists include thapsigargin, ionomycin, CPA, DBHQ, and/or A23187, while preferred PRR activators include DAMPs, TLR ligands, and/or NOD ligands.

Therefore, in one aspect of the inventive subject matter, the inventors contemplate a method of improving healing of a sterile or TLR/NOD ligand-poor wound that includes a step of administering a CFA and a PRR ligand to a patient under a protocol that ensures contemporaneous presence of at least some of the administered CFA and PRR ligand at the wound in an amount effective to improve healing of the wound. While not wishing to be bound by any theory or hypothesis, the inventors contemplate that stimulation of one or more PRR-associated pathways is amplified by the CFA to so improve one or more aspects of wound healing (e.g., reduced time to closure of a surface wound, reduced incidence of infection of the wound, and increased tissue remodeling within the wound). Preferably, the CFA and the PRR ligand are present and/or administered in synergistic quantities with respect to the improvement of the wound healing.

In some aspects of the inventive subject matter, the CFA is a sarco/endoplasmic reticulum $Ca^{2+}$-ATPase (SERCA) inhibitor and/or a calcium ionophore (e.g., ionomycin, calcimycin, cyclopiazonic acid (CPA), 2,5-di-tert-butylhydroquinone (DBHQ), A23187, thapsigargin, etc.), while the PRR ligand is a TLR or a NOD ligand, and preferred ligands include a DAMP ligand, an endogenous ligand, a high-mobility group box-1 protein, a heat shock protein, a component of extracellular matrix, or an oligosaccharide derived from hyaluronic acid or heparan sulfate, or Pam2Cys, polyI:C, endotoxin, flagellin, imiquimod, CpG-containing DNA, C12-iE-DAP, or muramyl dipeptide.

It is further contemplated that the CFA and the PRR ligand are present in a single formulation for topical administration, or that at least one of the CFA and PRR ligand are coupled to the surface of a medical item for wound treatment (e.g., a suture, a staple, a clamp, an implant, or wound dressing). Thus, the protocol may comprise directly and contemporaneously contacting the wound with the CFA and the PRR ligand, or topical administration to the wound and/or exposing the wound to a medical item for wound treatment to which the CFA and PRR are coupled. While not limiting to the inventive subject matter, it is further contemplated that the wound may be produced by a surgical procedure, or is a traumatic injury without an acute or persistent infection. As used herein, and unless the context dictates otherwise, the term "coupled to" is intended to include both direct coupling (in which two elements that are coupled to each other contact each other) and indirect coupling (in which at least one additional element is located between the two elements). Therefore, the terms "coupled to" and "coupled with" are used synonymously.

Therefore, and viewed from a different perspective, the inventors also contemplate a method of treating a sterile or TLR/NOD ligand-poor wound that include a step of administering to the wound a pattern recognition receptor (PRR) ligand to produce at the wound site a non-saturating stimulus for a TLR and/or NOD signaling pathway, and a further step of administering to the wound a CFA patient in an amount effective to amplify the stimulus. Most typically, amplification of the stimulus is performed under a protocol that will improve healing of the wound.

As noted before, it is contemplated that the CFA is a SERCA inhibitor and/or a calcium ionophore, and/or that the PRR ligand is a TLR ligand, a NOD ligand, a DAMP ligand, or an endogenous ligand. Likewise, it is contemplated that the CFA and PRR ligand are topically administered to the wound, or that the CFA and PRR ligand are coupled to the surface of a medical item for wound treatment, and that administration is performed by contacting the wound with the medical item.

Various objects, features, aspects and advantages of the present invention will become more apparent from the following detailed description of preferred embodiments of the invention.

BRIEF DESCRIPTION OF THE DRAWING

FIG. 2B: Ionomycin; FIG. 2C: Cyclopiazonic acid; FIG. 2D: DBHQ; FIG. 2E: Thapsigargin) and exemplary TLR and NOD ligands for respective TLR and NOD receptors with respect to strength of IL-8 production.

DETAILED DESCRIPTION

Figure 1:
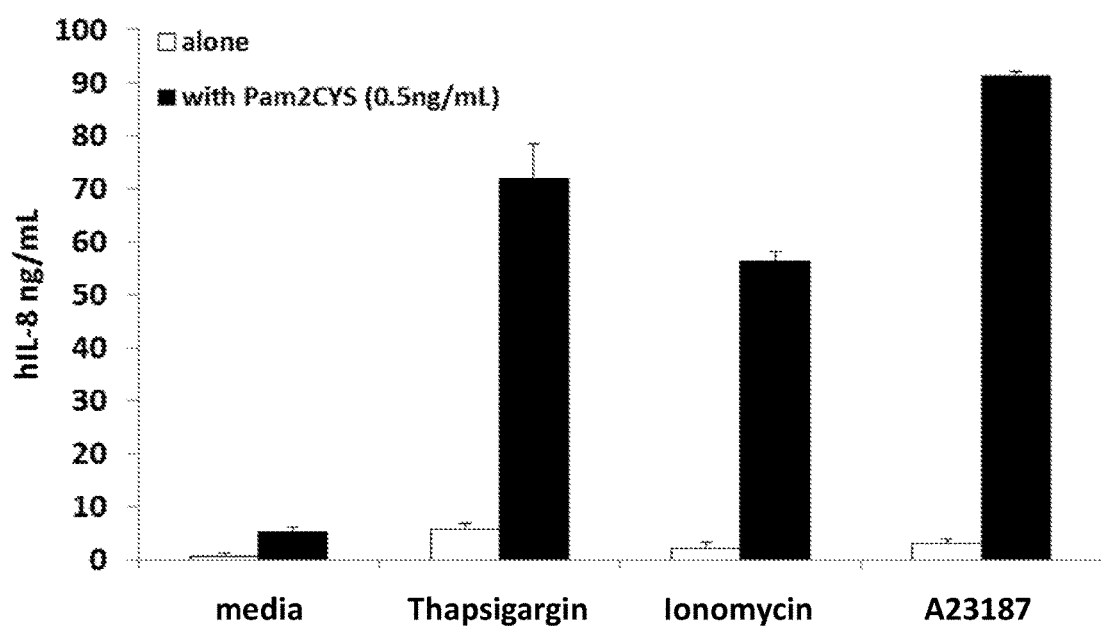
FIG. 1 is an exemplary graph depicting synergistic effect of various calcium flux agonists with an exemplary TLR ligand (Pam2CYS).

The inventors have previously noted that certain TLR and NOD family members can act in a capacity of mediators of inflammation and immune activation in vaccine and autoimmunity settings. Based on these and other findings, the inventors previously used CFA to amplify one or more TLR/NOD ligand signals that were present in a wound due to bacterial infections to so increase the immune response against the bacteria, and combat infection with concomitant reduction of time-to-closure of the wound.

More particularly, the inventors have recently identified various CFA (e.g., thapsigargin, cyclopiazonic acid (CPA), 2,5-di(tert-butyl) hydroquinone (DBHQ), A23187, and ionomycin) that exhibit potent immune-modulating activity by amplifying TLR and NOD-based signals. For example, the inventors showed that treatment of mouse skin with CFA prior to administration of live S. aureus bacteria resulted in significant decreases in bacterial load and wound healing time due to an increased immune response. Details, further considerations, compositions, and methods suitable for use in the inventive subject matter presented herein are provided in our copending International application with the serial number PCT/US2013/069939, filed 13 Nov. 2013, which is incorporated in its entirety by reference herein.

The inventors now recognized that improved wound healing, and especially reduced time to closure of a superficial wound, reduced incidence of infection of the wound, and/or increased tissue remodeling within the wound (e.g., reduced fibrosis/scar formation) can be achieved in sterile wounds or wounds that present a TLR/NOD ligand-poor environment by treatment of the wound contemporaneously with a TLD/NOD ligand or ligand analog and CFA. In that context, it should be appreciated that members of both PRR protein families have been implicated in other biological processes such as angiogenesis and/or tissue remodeling following recognition of their respective ligands. Thus, amplification of signals from one or more TLD/NOD ligands or ligand analog binding in the associated pathways via CFA is contemplated to provide similar (synergistic) effects as observed with wound infection with organisms comprising TLD/NOD ligands. While not limiting to the inventive subject matter, it is contemplated that the improved wound healing occurs in a manner that is independent of immune stimulation but may involve mechanisms associated with tissue repair/remodeling.

In light of these findings and other experiments (data not shown here) the inventors now contemplate that exposure of injured tissues, and particularly sterile wounds or traumatic injuries without acute infection to formulations containing CFA and/or PRR ligands and analogs thereof can be used to reduce wound healing time, reduce inflammation, reduce scar formation/fibrosis, and stimulate tissue remodeling. Moreover, contemplated compositions and methods are also deemed to activate innate immune cells to prevent or limit microbial and/or viral infection.

Therefore, the inventors contemplate use of CFA and PRR ligands and/or analogs thereof for use in compositions and methods to treat sterile wounds and/or other traumatic injuries that present a TLR/NOD ligand-poor environment (i.e., environment where TLR/NOD pathway is not activated by pathogen or ligand, or activated to a degree that is less than 20% of maximum activation). Viewed from a different perspective, the inventors contemplate that use of CFA and PRR ligands and analogs thereof is particularly effective in stimulating healing and/or preserving health of injured tissues that are exposed to the CFA and PRR ligands. For example, a mammal (and preferably a human) can be exposed to a therapeutic or prophylactic quantity of a CFA and PRR ligand to reduce scar formation, improve time and/or completeness of wound closure, host control of microbial and/or viral infection, and/or reduce inflammation at the site of injury. Thus, and at least in some instances, it is contemplated that the CFA and/or PRR ligands do not directly interfere with a microbe or virus in or at the wound, but stimulate a host response that is effective to promote wound healing and to control presence and/or propagation of the microbe or virus.

Among other suitable choices, particularly contemplated CFA will include one or more calcium ionophores, preferred agonists include ionomycin, calcimycin, beauvericin, calcium ionophore II, calcium ionophore IV, calcium ionophore V, and calcium ionophore VI. Further contemplated CFA also include various SERCA inhibitors, and especially preferred SERCA inhibitors include DBHQ, thapsigargin, CPA, ruthenium red, gingerol, and paxilline. In further preferred aspects, the CFA will include thapsigargin, A23187, ionomycin, DBHQ, and/or CPA.

Likewise, the nature of the PRR ligand may vary considerably, however, it is generally preferred that the PRR ligand will be a TLR and/or NOD ligand. Thus, and viewed from a different perspective, suitable PRR ligands include various DAMPs and PAMPs, and especially various bacterial glycolipids, lipopeptides and lipoproteins, lipoteichoic acid, double stranded RNA, lipopolysacchlides, fibrinogen, heparin sulfate and hyaluronic acid fragments, flagellin, etc. Thus, exemplary PRR ligands will include Pam2Cys, polyI: C, endotoxin, imiquimod, CpG-containing DNA, C12-iE-DAP, and muramyl dipeptide. Most of these ligands are commercially available (e.g., Enzo Life Sciences, 5120 Butler Pike, Plymouth Meeting, Pa. 19462) or can be prepared using protocols well known in the art. Likewise, using the known ligands, analogs can be prepared in a synthetic or semi-synthetic manner.

Of course, it should be appreciated that (where appropriate) contemplated compounds may have one or more asymmetric centers or groups that may give rise to isomeric, tautomeric, or other steric isoforms (e.g., R-, and/or S-configuration, E/Z configuration, tautomeric isoforms, enantiomers, diastereomers, etc.), and each of such forms and mixtures thereof are expressly contemplated herein. Additionally, it should be appreciated that contemplated calcium flux agonists may be chemically modified to achieve a desired physicochemical parameter (e.g., solubility in aqueous solvents, membrane permeability, selectivity towards Ca2+, etc.) Therefore, and as already noted above, suitable calcium flux agonists may be fully synthetic, semi-synthetic, or isolated from host strains producing such ionophores.

Moreover, contemplated compounds may also be converted to prodrugs to increase delivery and/or target specificity to an affected tissue or organ. The term "prodrug" as used herein refers to a modification of contemplated compounds, wherein the modified compound exhibits less pharmacological activity (as compared to the unmodified compound) and wherein the modified compound is converted within a target cell or target organ back into the unmodified form. For example, conversion of contemplated compounds into prodrugs may be useful where the active drug is too toxic for safe systemic administration, or where the contemplated compound is poorly absorbed by the digestive tract, or where the body breaks down the contemplated compound before reaching its target. There are numerous methods for the preparation of prodrugs known in the art, and all of those are contemplated herein. For example, suitable prodrug approaches are described in Prodrugs (Drugs and the Pharmaceutical Sciences: a Series of Textbooks and Monographs) by Kenneth B. Sloan (ISBN: 0824786297), or in Hydrolysis in Drug and Prodrug Metabolism: Chemistry, Biochemistry, and Enzymology by Bernard Testa (ISBN: 390639025X), which are to the appropriate extent incorporated by reference herein.

Similarly, it should be noted that contemplated compounds may also be less active in the form as described herein, and be more active as metabolite or metabolites that are formed in vivo. For example, contemplated compounds may be transformed by the hepatic phase I and/or phase II enzyme system, or by gastric acidity, intestinal microbial environment, or other biochemical process. Thus, suitable compounds may be oxidized, hydroxylated, ligated to a carbohydrate, etc.

With respect to contemplated compositions it is generally preferred that the calcium flux agonists and the PRR ligands are provided in a composition that is suitable for delivery to a cell or tissue. Such compositions may include the CFA and the PRR ligand together, or two separate compositions may be prepared for independent administration. However, it is preferred that where administration is separate, the CFA and the PRR ligand are provided under a protocol that delivers effective quantities of the CFA and the PRR to the wound or injured tissue in an at least overlapping timeframe. Furthermore, it should be noted that while it is preferred to use the same route of administration (e.g., topical or direct contact), the CFA may also be delivered in a route that is different from the route of administration for the PRR ligand. For example, while the CFA may be administered topically, the PRR ligand may be injected or orally administered.

In particularly preferred aspects, the CFA and/or PRR are topically administered using a spray, cream, or medical item for wound treatment (e.g., suture, staple, clamp, implant, wound dressing (e.g., gauze, band aid, films, occlusive covers, alginate or other colloid dressings, etc.). However, numerous alternative manners of administration are also deemed suitable and include injection, oral administration, pulmonary administration, and other parenteral routes.

Therefore, especially suitable compositions will include liquid compositions, gels, solid compositions, all of which may be associated or coupled to a carrier, or applied directly to the cell or tissue. Most typically, such compositions will include an aqueous solvent or otherwise pharmaceutically acceptable carrier together with one or more calcium flux agonists and one or more PRR ligand or ligand analog. In particularly preferred aspects of the inventive subject matter, the pharmaceutical composition is formulated for topical application to an injured or infected tissue, more preferably epithelial tissue, and most preferably skin. Alternatively, or additionally, it is also especially contemplated that the calcium flux agonist and one or more PRR ligand or ligand analog are coupled to a surgical article, most typically in form of a coating, or impregnation. Regardless of the manner of coupling, it should be appreciated that the surgical article will be in direct contact to the tissue (typically tissue injured by incision, cauterization, resection, etc). For example, the calcium flux agonists and one or more PRR ligand or ligand analog may be present on the surface or embedded in a polymeric film (which may or may not be degradable or erodible) to so provide improvement to wound healing at the site of injury.

With respect to suitable quantities of the CFA and PRR ligand, it is generally preferred that the CFA and PRR ligand are present in an amount that improves at least one parameter of wound healing (e.g., reduce wound healing time, inflammation, scar formation/fibrosis, and/or stimulate tissue remodeling) upon application of the formulation to the wound. It is still further preferred that the calcium flux agonist is present in an amount that synergistically enhances the PRR signaling as compared to signaling with a single compound only.

With respect to suitable routes of administration, it should be noted that the compositions according to the inventive subject matter may be administered in various manners, including topically, nasally, by inhalation, orally, parenterally, etc. wherein the term "parenteral" as used herein includes subcutaneous, intravenous, intramuscular, intraarticular, intrasynovial, intrathecal, intrahepatic, intralesional, and intracranial administration (typically injection or infusion). Most preferably, however, the compositions are administered topically in a liquid, gel, or solid form, or via direct contact with a medical article to which the composition of the inventive subject matter is coupled (e.g., on the surface via coating or impregnation). For example, contemplated pharmaceutical compositions may be administered topically to areas or organs readily accessible by topical application, including the eye, the skin, the lower intestinal tract, open or closed wounds, or areas exposed during surgical intervention. There are numerous topical formulations known in the art, and all of such formulations are deemed suitable for use herein.

For example, contemplated compositions may be formulated in an ointment containing the active component suspended or dissolved in one or more carriers. Carriers for topical administration of the compounds of this invention include mineral oil, liquid petrolatum, white petrolatum, propylene glycol, polyoxyethylene, polyoxypropylene compound, emulsifying wax and water. Alternatively, the pharmaceutical compositions can be formulated in a suitable lotion or cream containing the active components suspended or dissolved in a pharmaceutically acceptable carrier. Suitable carriers include mineral oil, sorbitan monostearate, polysorbate 60, cetyl esters wax, cetearyl alcohol, 2-octyldodecanol, benzyl alcohol and water. As at least some of the active compounds are highly hydrophobic, it is contemplated that the formulation will take into account relatively poor solubility and thus may be prepared as an emulsion, as nanovesicular particles, or administered in a hydrophobic base under occlusion.

As already noted above, it should be appreciated that while contemplated compounds and compositions may be applied topically or in a pharmaceutical composition (e.g., cream, ointment, etc.) numerous alternative methods of application to the affected tissue are also deemed suitable. For example, contemplated compositions may be coupled to or incorporated into a carrier that is directly and reversibly applied to the site of treatment, or that is implanted or otherwise placed in proximity or contact with the treatment site. For example, contemplated compounds and compositions may be incorporated into one or more portions of topically applied and removable carriers (e.g., bandages, gauze, etc.) or into covering films that may or may not dissolve or erode (e.g., via biodegradable drug-eluting polymers). Alternative carriers include beads or biodegradable drug-eluting polymers that are implanted wherein contemplated compounds and compositions may be part of the surface of the implanted device or coated onto such devices.

Alternatively, contemplated formulations may also be injected into skin or other site of administration. Most preferably, sterile injectable forms of contemplated compounds will include emulsions, aqueous solutions, or oleaginous suspensions. These suspensions may be formulated according to techniques known in the art using suitable dispersing or wetting agents and suspending agents. The sterile injectable preparation may also be prepared as a sterile injectable solution or suspension in a non-toxic parenterally acceptable diluent or solvent, for example as a solution in 1,3-butanediol. Among other acceptable vehicles and solvents, especially contemplated liquids include water, Ringer's solution, and isotonic sodium chloride solution. In addition, sterile, fixed oils may be employed as a co-solvent or suspending medium (e.g., natural or synthetic mono- or diglycerides). Fatty acids may also be used, and suitable fatty acids include oleic acid and its glyceride derivatives, olive oil, castor oil, especially in their polyoxyethylated versions. Such oil solutions or suspensions may further contain a long-chain alcohol diluent or dispersant.

In another example, contemplated compounds may be orally administered in any orally acceptable dosage form, including capsules, tablets, aqueous suspensions, or solutions. In the case of tablets for oral use, all pharmaceutically acceptable carriers (e.g., lactose, corn starch, etc) are deemed suitable. Similarly, various lubricating agents may be added (e.g., magnesium stearate). For oral administration in a capsule form, useful diluents include lactose and dried corn starch.

With respect to the amount of contemplated compounds in the composition, it should be recognized that the particular quantity will typically depend on the specific formulation, active ingredient, and desired purpose. Therefore, it should be recognized that the amount of contemplated compounds will vary significantly. However, it is generally preferred that the compounds are present in a minimum amount effective to deliver prophylactic and/or therapeutic effect in vitro and/or in vivo. Viewed from another perspective, the calcium flux agonist is present in an amount effective to promote various aspects of wound healing (e.g., reduced time to closure of a surface wound, reduced incidence of infection of the wound, and increased tissue remodeling within the wound).

Moreover, while not limiting to the inventive subject matter, it is generally preferred that the calcium flux agonist is provided to the cell or tissue such that the agonist will be present in the cell (in the presence of the TLR or NOD ligand) at a suboptimal concentration with respect to a maximum effect of the calcium flux agonist in the absence of the ligand. In this context, it should be noted that the suboptimal concentration of the calcium flux agonist is a concentration that is well below the maximum response (e.g., with respect IL-8 production) obtainable with the calcium flux agonist. Thus, sub-optimal concentration of the calcium flux agonist will be concentration that will provide equal or less than 80%, equal or less than 70%, equal or less than 60%, between 20-60%, or between 10-50% of the dosage that provides a maximum effect (with respect to IL-8 production) for that calcium flux agonist. For example, an exemplary suboptimal concentration for thapsigargin is between 10-50 nM (e.g., about 20 nM), which is well below a maximum effect obtainable for thapsigargin. Likewise, an exemplary suboptimal concentration for A23187 is between 100-500 nM (e.g., about 316 nM), which is well below a maximum effect obtainable for A23187, and an exemplary suboptimal concentration for ionomycin is between 300 nM-5 µM (e.g., about 1 µM), which is well below a maximum effect obtainable for ionomycin. Viewed from another perspective, suboptimal concentrations will therefore be characterized as concentrations below which an acute toxic effect can be observed for a cell or tissue exposed to the calcium flux agonist.

A maximum response and suboptimal concentrations can be readily determined using an IL-8 ELISA test and/or a luminescence test as described in our International application with the serial number PCT/US2013/069939, filed 13 Nov. 2013, which is incorporated in its entirety by reference herein. In preferred aspects of the inventive subject matter, the suboptimal concentration will be a concentration at which the response is equal or less than 70% of the maximum response, more typically equal or less than 50% of the maximum response, and most typically equal or less than 30% of the maximum response. Thus, suboptimal concentrations will be in the range of between 1-20% of the maximum response, between 20-40% of the maximum response, between 40-60% of the maximum response, between 60-80% of the maximum response, or between 80-95% of the maximum response. Likewise, it is noted that the PRR ligand may also be present in a suboptimal concentration, and the suboptimal concentration will be a concentration at which the response to the ligand is equal or less than 70% of the maximum response, more typically equal or less than 50% of the maximum response, and most typically equal or less than 30% of the maximum response for the ligand alone. Thus, suboptimal concentrations will be in the range of between 1-20% to 1-40% of the maximum response, between 20-40% to 20-80% of the maximum response, between 30-70% of the maximum response, between 40-80% of the maximum response, or between 50-95% of the maximum response for the ligand alone. Unless the context dictates the contrary, all ranges set forth herein should be interpreted as being inclusive of their endpoints and open-ended ranges should be interpreted to include only commercially practical values. Similarly, all lists of values should be considered as inclusive of intermediate values unless the context indicates the contrary.

Consequently, in at least some embodiments, contemplated compounds are present in an amount of between about 0.1 ng/ml to about 100 mg/ml, more typically in an amount of between about 10 ng/ml to about 10 mg/ml, and most typically between about 1 µg/ml to about 100 µg/ml. Where the formulation is a solid or a gel, contemplated compounds will be present in an amount of between about 0.1 ng/g to about 100 mg/g, more typically in an amount of between about 10 ng/g to about 10 mg/g, and most typically between about 1 µg/g to about 100 µg/g. Viewed from a different perspective, the calcium flux agonist will typically be present in the formulation at a concentration of between 0.1 µM to 10 µM, between 10 µM to 100 µM, between 100 µM to 1 mM, between 1 mM to 10 mM, or between 10 mM to 100 mM.

Additionally, and with respect to the concentration of the calcium flux agonist at the cell or tissue ("effective exposure concentration"), it is generally preferred that the effective exposure concentration will be between 1 pM and 1 mM, and most preferably at a suboptimal concentration for the respective calcium flux agonist. Therefore, thapsigargin will typically have an effective exposure concentration of between 1 nM to 1 µM, more typically between 1 nM to 500 nM, and most typically between 1 nM to 50 nM, while DBHQ and CPA will typically have an effective exposure concentration of between 100 nM to 500 µM, more typically between 500 nM to 100 µM, and most typically between 1 µM to 50 µM. On the other hand, ionomycin and A23187 will typically have an effective exposure concentration of between 10 nM to 100 µM, more typically between 100 nM to 50 µM, and most typically between 200 nM to 10 µM.

Therefore, suitable amounts of contemplated compounds will be in the range of 0.1 µg per dosage unit to about 0.5 gram per dosage unit, more typically between 10 µg per dosage unit to about 0.05 gram per dosage unit, and most typically between 50 µg per dosage unit to about 100 mg per dosage unit. Thus, suitable dosages will be in the range of about 0.01 µg/kg and 100 mg/kg, more typically between 1 µg/kg and 50 mg/kg, and most typically between 10 µg/kg and 10 mg/kg.

In one typical example of contemplated pharmaceutical compositions, the inventors contemplate a composition that is formulated for topical application (e.g., as spray, as ointment, or as solution with pharmaceutically acceptable carrier) and that includes a CFA and a PRR ligand in conjunction with a pharmaceutical carrier, wherein the CFA and PRR ligand are present in a therapeutically effective concentration. For example, contemplated compositions may include one or more of thapsigargin, cyclopiazonic acid (CPA), 2,5-di(tert-butyl) hydroquinone (DBHQ), A23187, and ionomycin at a concentration of between 0.1-10 ng/g (or ml) of formulation, 10-1000 ng/g (or ml) of formulation, 1-100 mcg/g (or ml) of formulation, 0.1-10 mg/g (or ml) of formulation, and even higher. On the other hand, especially preferred PRR ligands include TLR/NLR ligands, and particularly Pam2Cys, polyI:C, endotoxin, flagellin, imiquimod, CpG-containing DNA, C12-iE-DAP, and/or muramyl dipeptide. As already noted above, especially preferred concentrations will typically be between 0.1-10 ng/g (or ml) of the formulation, 10-1000 ng/g (or ml) of the formulation, 1-100 mcg/g (or ml) of the formulation, 0.1-10 mg/g (or ml) of the formulation, and even higher.

Moreover, it should be appreciated that the molar ratio of administered CFA to PRR will vary considerably, and the particular type of CFA and PRR will dictate at least in part the relative quantities used. However, it is typically preferred that the molar ratio of administered CFA to PRR is between 1:1000, and 1:100, or between 1:100 and 1:10, or between 1:10 to 1:1, or between 10:1 and 1:1, or between 100:1 to 10:1, or between 1000:1 and 100:1. Therefore, it should be appreciated that the patient will receive per administration a quantity of the CFA of at least 0.1-10 ng, at least 10-1000 ng, at least 1-100 mcg, at least 0.1-10 mg, and even more. Likewise, it is contemplated that the patient will receive per administration a quantity of the PRR ligand of at least 0.1-10 ng, at least 10-1000 ng, at least 1-100 mcg, at least 0.1-10 mg, and even more.

Suitable schedules of administration may vary considerably. However, it is especially preferred that where a CFA and a PRR ligand are administered, administration route and schedule are selected such that both CFA and the PRR ligand are present at the target tissue for at least overlapping periods of time. Thus, simultaneous administration is typically preferred, but not exclusively contemplated.

With respect to contemplated modes of action, and without wishing to be bound by any particular theory or hypothesis, the inventors therefore contemplate that the co-administered PRR ligand will activate at the target tissue a cell signaling pathway relevant to wound healing that is further amplified by administration of the CFA. Thus, by amplification of one or more PRR pathway signals using the CFA, the inventors contemplate that wound healing of the mammal under treatment will be enhanced to so, for example, reduce wound healing time, to suppress and/or reduce microbial/viral infection, and/or reduce inflammation.

Contemplated Experiments

The following examples are for guidance only and not meant to limit the scope of the inventive subject matter presented herein. The PHOSITA will be readily able to choose the appropriate animal host system.

Appropriate animal systems in consideration may be treated with such formulations prophylactically (prior to surgery or wound creation) or therapeutically (following surgery or wound creation), and wound healing will be scored using model-specific criteria and resulting data will be evaluated using appropriate statistical tools. Based on the so obtained results, appropriate treatment protocols and regimens can be developed for human use without undue experimentation. Consequently, and based on the critical importance of PRR to the processes surrounding wound healing and inflammation, the inventors therefore expect that formulations containing CFA together with one or more PRR ligands will provide significant benefit to the host in these disease settings. Among other contemplated wounds suitable for treatment with the compositions and methods described herein, surgical wounds, traumatic injuries (e.g., cuts, gunshot, shrapnel, etc.), superficial injuries (e.g., abrasion, tears, bruises, etc) are particularly contemplated herein. Moreover, while not limiting to the inventive subject matter presented herein, it is generally preferred that the wounds and/or injuries are sterile or at least have no acute or persistent infection, but may be subject to inflammation.

For example, the inventors contemplate that individual CFA compounds can be tested (e.g., thapsigargin, A23187, ionomycin, DBHQ, CPA) alone and in combination with one or more TLR/NLR ligands (with particular emphasis on Pam2Cys, polyI:C, endotoxin, flagellin, imiquimod, CpG, C12-iE-DAP, and MDP which are ligands for TLR2, TLR3, TLR4, TLR5, TLR7, TLR9, NOD1, and NOD2, respectively) in an appropriate wound repair model such as those provided by the mouse and porcine model systems. Viewed from a different perspective, the inventors also contemplate that individual CFA compounds can be tested alone and/or in combination with one or more DAMP (e.g., bacterial endotoxin, di- and tri-acylated peptides, viral double stranded RNA, flagellin, imiquimod, CpG containing DNA, etc.) and/or PAMP (e.g., HMGB1, HSP22, HSP70, HSP72, gp96, biglycan, tenascin-C, versican, oligosaccharides derived from hyaluronic acid or heparan sulfate, etc.).

For example, a splinted excisional wound healing mouse model can be used that closely parallels human wound healing which allows wound healing to occur through granulation and re-epithelization. On day −1, the hair on the animal's dorsal side will be shaved using clippers followed by application of a depilatory agent (Nair; Church & Dwight Co) to remove any remaining hair. A dime size amount of Nair will be placed on shave area for 30 seconds, and wiped away with sterile gauze. At this time animals will be split into two groups, ones with CFA pretreatment prior to wound excision and ones which will receive formulations containing CFA post wound excision. On day 0, animals will undergo surgery under isoflurane anesthesia where symmetrical wounds will be patterned on the shaved area using a 5-mm leather punch (one on each side of the midline). A donut-shaped press to seal silicone splint (Sigma-Aldrich) with a diameter two times that of the wound will be placed with the wound centered within the splint. Immediate-bonding adhesive (e.g., alkyl cyanoacrylate, Kragle, etc.) will be used to fix the splint to the skin followed by 4-0 nylon sutures to ensure position. Excision wounds on animals in both groups will receive additional formulations containing sham or combinations of TLR and/or NOD ligands at this time.

Preferred TLR ligands are Pam2Cys, heat killed *S. aureus*, poly I:C, endotoxin, flagellin, imiquimod, CpG DNA, as well as multi-TLR ligand containing formulations, while preferred NOD ligands include C12-iE-DAP and muramyl dipeptide (MDP) for NOD1 and NOD2, respectively. A single tegaderm (3M) wrap will be used to keep the wounds covered, and wrapping will be changed when pictures are taken. All animals will have their nails clipped as well on Day 0 and Day 7 to prevent removal of splints. Animals will then be caged individually. All procedures will be performed under a BioBubble Hood (Class 2).

While mice are under isoflurane anesthetic, digital photographs will be taken using a digital camera (Nikon) on Days 0, 3, 7, 10, and 14 (terminal). Wound size will be determined by pixel counts in outlined areas with the pixel count of the splint around each wound will be used as a reference since the area will not change throughout the study. Wound closure will be reported as the percentage closed as compare to Day 0's pixel count: % closed=[(area on Day 0−open area on final Day)/area on Day 0]×100. Time to closure will be defined as the time at which the wound bed has completely filled in with the new tissue, or when the wound area is equal to zero.

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

The present inventive subject matter is drawn to various compositions and methods of calcium flux agonists in which these compounds are used to modulate an immune response to a TLR- or NOD-mediated event, and especially to synergistically increase responses to TLR and/or NOD ligand binding. Notably, synergistic effect with respect to immune stimulation is observed where the calcium flux agonist is present in suboptimal concentrations.

In one aspect of the inventive subject matter, the inventors contemplate use of a calcium flux agonist to enhance an immune response of an immune competent cell to a ligand of a pattern recognition receptor. For example, where the calcium flux agonist is a calcium ionophore, preferred agonists include ionomycin, calcimycin, beauvericin, calcium ionophore II, calcium ionophore IV, calcium ionophore V, and calcium ionophore VI, and where the agonist is a SERCA inhibitor, preferred SERCA inhibitors include DBHQ (2,5-di-tert-butylhydroquinone), thapsigargin, ruthenium red, gingerol, paxilline, and cyclopiazonic acid. Among other phenomena observable, the enhanced immune response is typically evidenced by an increased IL-8 secretion and/or an increased activation of NF-κB signaling, and it is preferred that the immune response is synergistically enhanced by the calcium flux agonist in the presence of the ligand, particularly where the calcium flux agonist is used at a suboptimal concentration (with respect to a maximum effect of the calcium flux agonist in the absence of the ligand).

In particularly preferred pharmaceutical compositions, the amount of the calcium flux agonist (e.g., ionomycin, calcimycin, or thapsigargin) synergistically enhances the immune response in the presence of the ligand as compared to the immune response in the absence of the ligand.

The inventors have discovered that calcium flux agonists that increase intracellular free $Ca^{2+}$ concentration (especially calcium ionophores and SERCA inhibitors) can be effectively used to modulate and/or enhance the immune response of a host to a TLR- or NOD-mediated event. In a particularly notable aspect, calcium flux agonists synergistically increased host responses to TLR and/or NOD ligand binding where the calcium flux agonist is present in a substantial suboptimal concentration.

Even more remarkable, very strong synergy between TLR and/or NOD activation and calcium flux agonists (ionophores/SERCA inhibitors) was observed for IL-8 production and activation of NF-κB signaling. For example, human promonocytic THP-1 cells were incubated in the presence or absence of a suboptimal dose of the TLR2 ligand Pam2CSK4 and compared to similarly treated cells which also received suboptimal doses of ionophore (here: A23187 and ionomycin). Interestingly and as further shown in more detail below, the inventors found that both agonists significantly increased the amount of IL-8 produced beyond the levels that would be produced if the individual responses were cumulative, thus indicating true synergy. In another example, κB-LUC THP-1 cells (a THP-1-derived transfectant line harboring an NF-κB-driven luciferase expression cassette) were cultivated in the presence or absence of a suboptimal dose of the TLR2 ligand Pam2CSK4 and compared to similarly treated cells that also received suboptimal doses of various SERCA inhibitors. Notably, and as also shown in more detail below, the inventors found that all of the tested agonists (here: thapsigargin, cyclopiazonic acid)

significantly increased the amount of luciferase produced beyond levels that would be produced if individual responses were cumulative and so once more indicate synergy.

For example, FIG. 1 is a graph depicting a typical synergistic effect selected calcium flux agonists with an exemplary TLR ligand. Here, the ionophores A23187 and ionomycin, as well as the SERCA inhibitor thapsigargin synergize with the TLR2 ligand (Pam2CYS) in the activation of cytokine release from the human THP-1 promonocytic leukemia cell line. It should be especially noted that while the TLR2 ligand alone provided for about 5 ng/ml IL-8 response, addition of a suboptimal dose of the calcium flux agonists (e.g. 20 nM for thapsigargin, 316 nM for A23187, and 1 µM for ionomycin) produced more than 10-fold quantities of IL-8 production in the cells.

To investigate if that observation was also true for other pattern recognition receptors, and especially for TLR and NOD receptors and other ligands, the inventors tested numerous TLR and NOD receptors and various ligands. Notably, as is evidenced from FIGS. 2A-3E, substantial synergy was observed across a large selection of types and classes of calcium flux agonists, as well as various TLR and NOD receptors and ligands, thus establishing that TLR- and NOD-mediated signals can be (typically synergistically) enhanced with suboptimal dosages of calcium flux agonists.

Figure 2A:
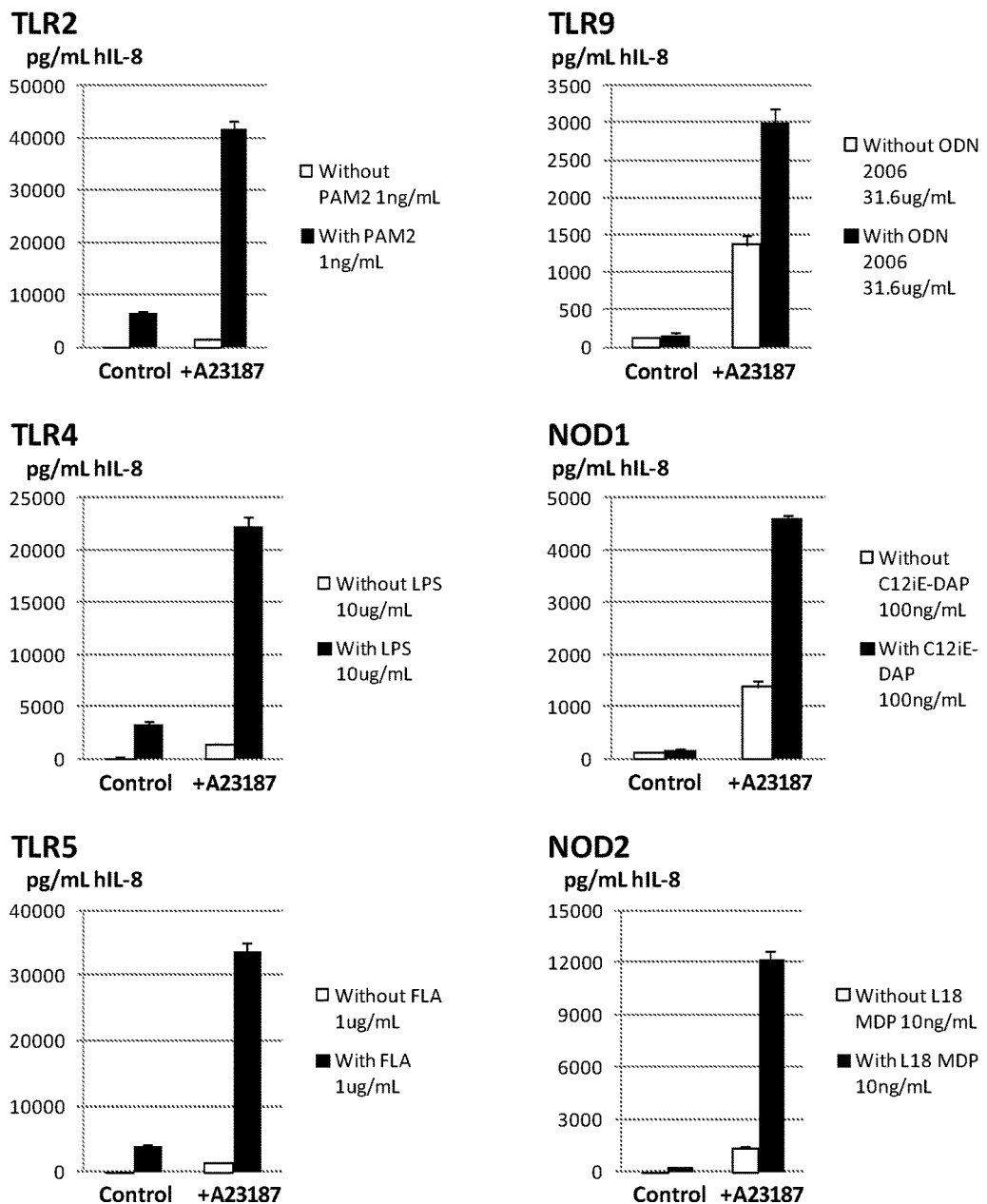
FIGS. 2A-2E show various graphs illustrating the synergistic effect of exemplary calcium flux agonists (FIG. 2A: A23187.
Figure 2B:
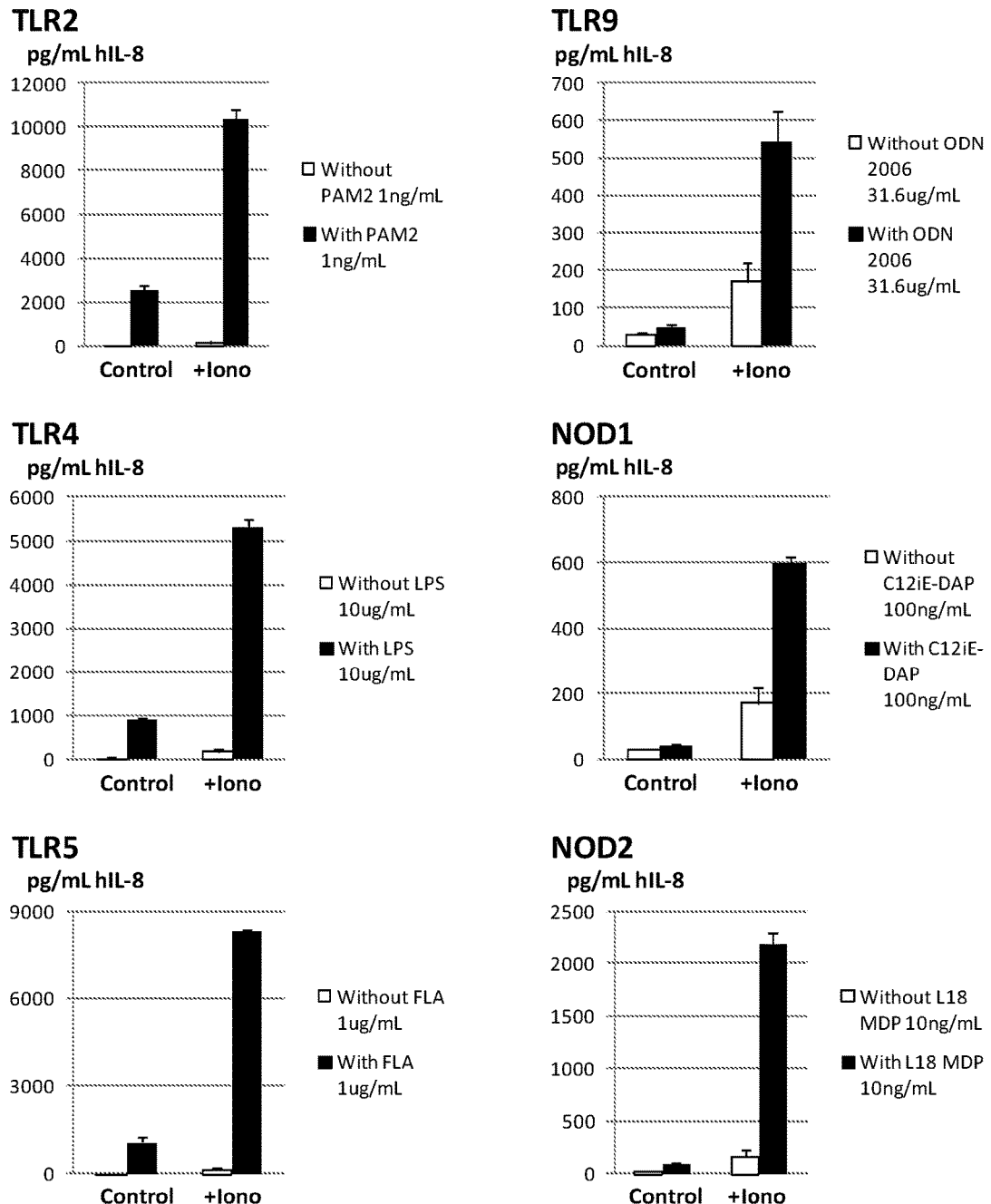
Figure 2C:
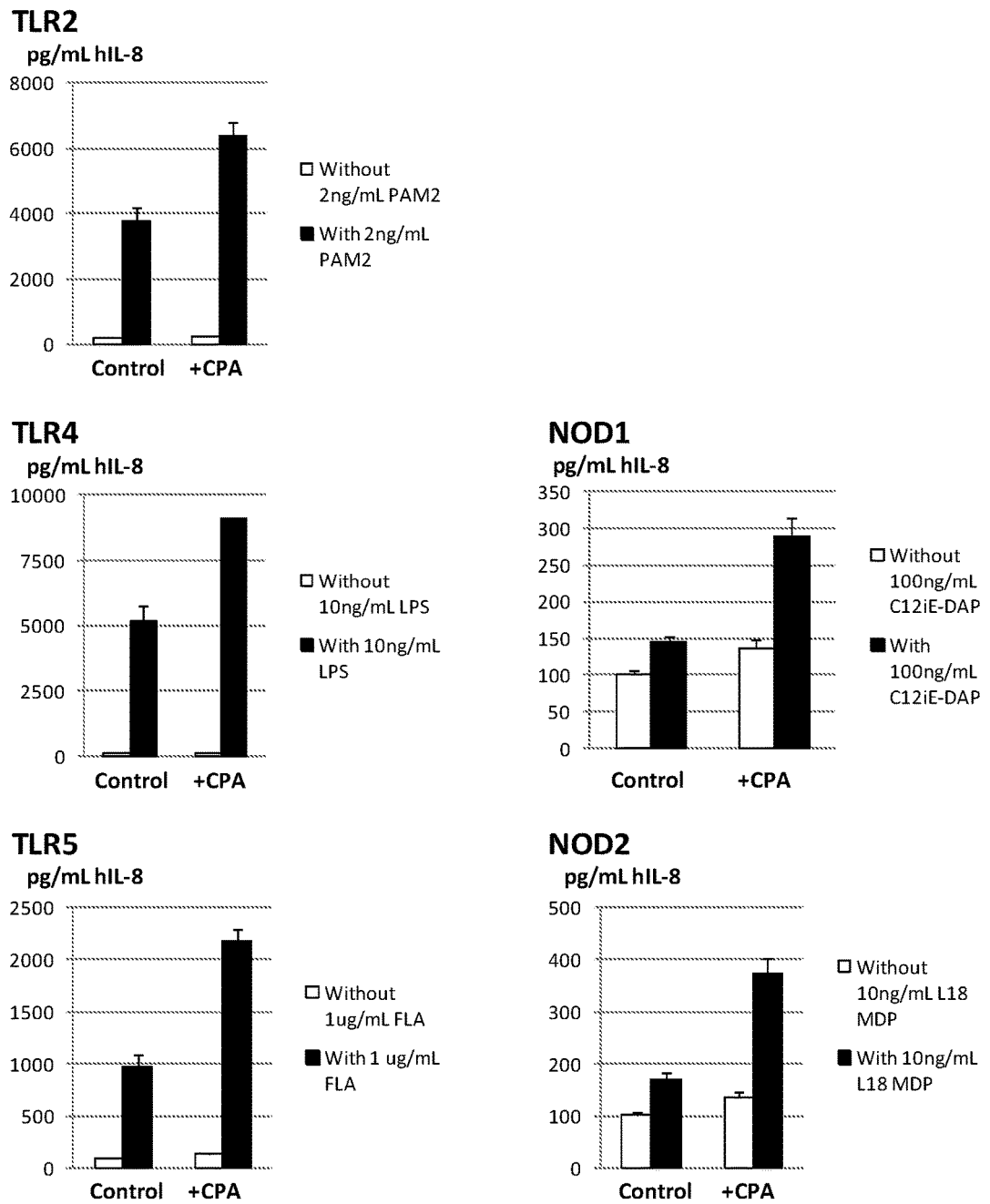
Figure 2D:
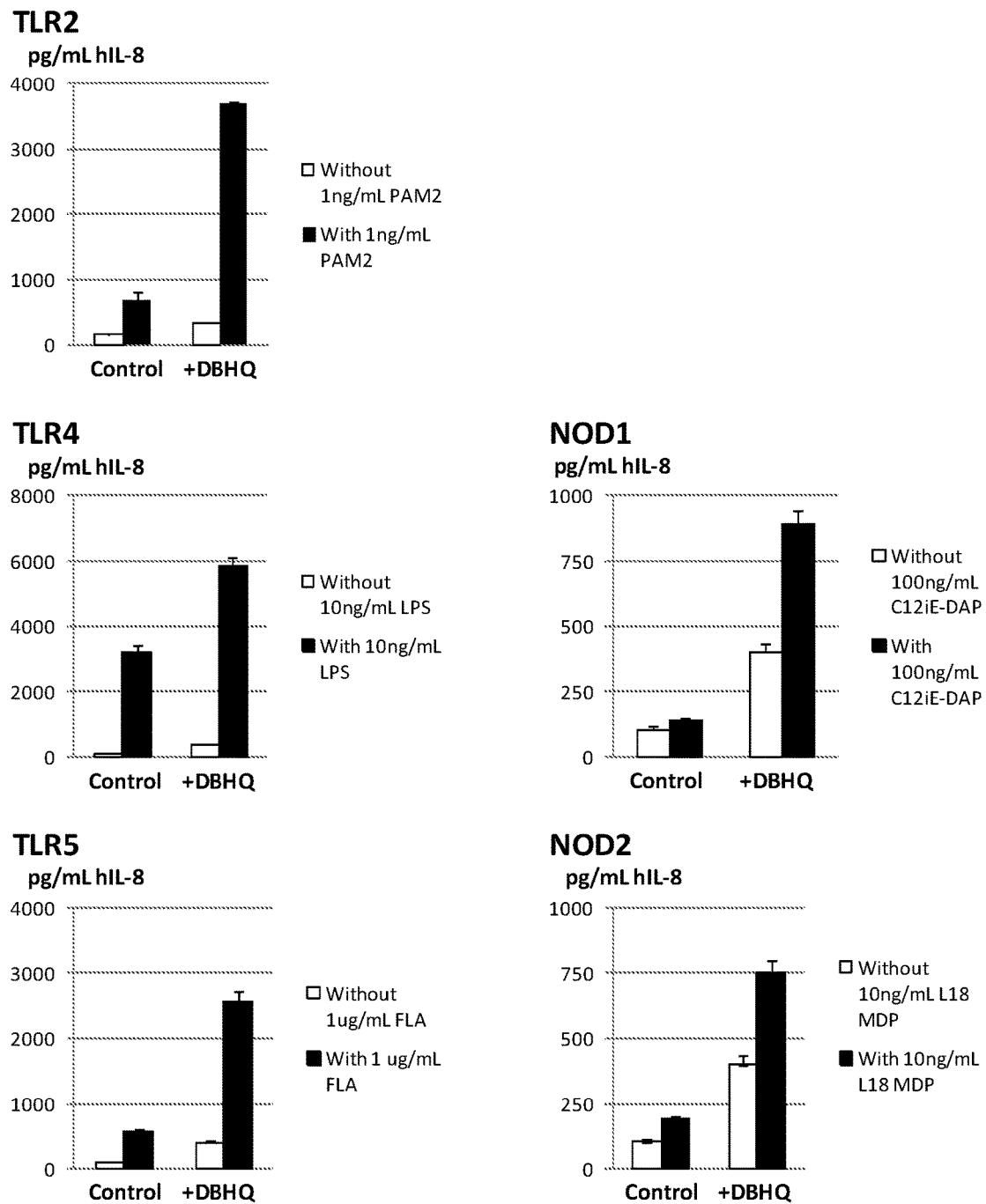
Figure 2E:
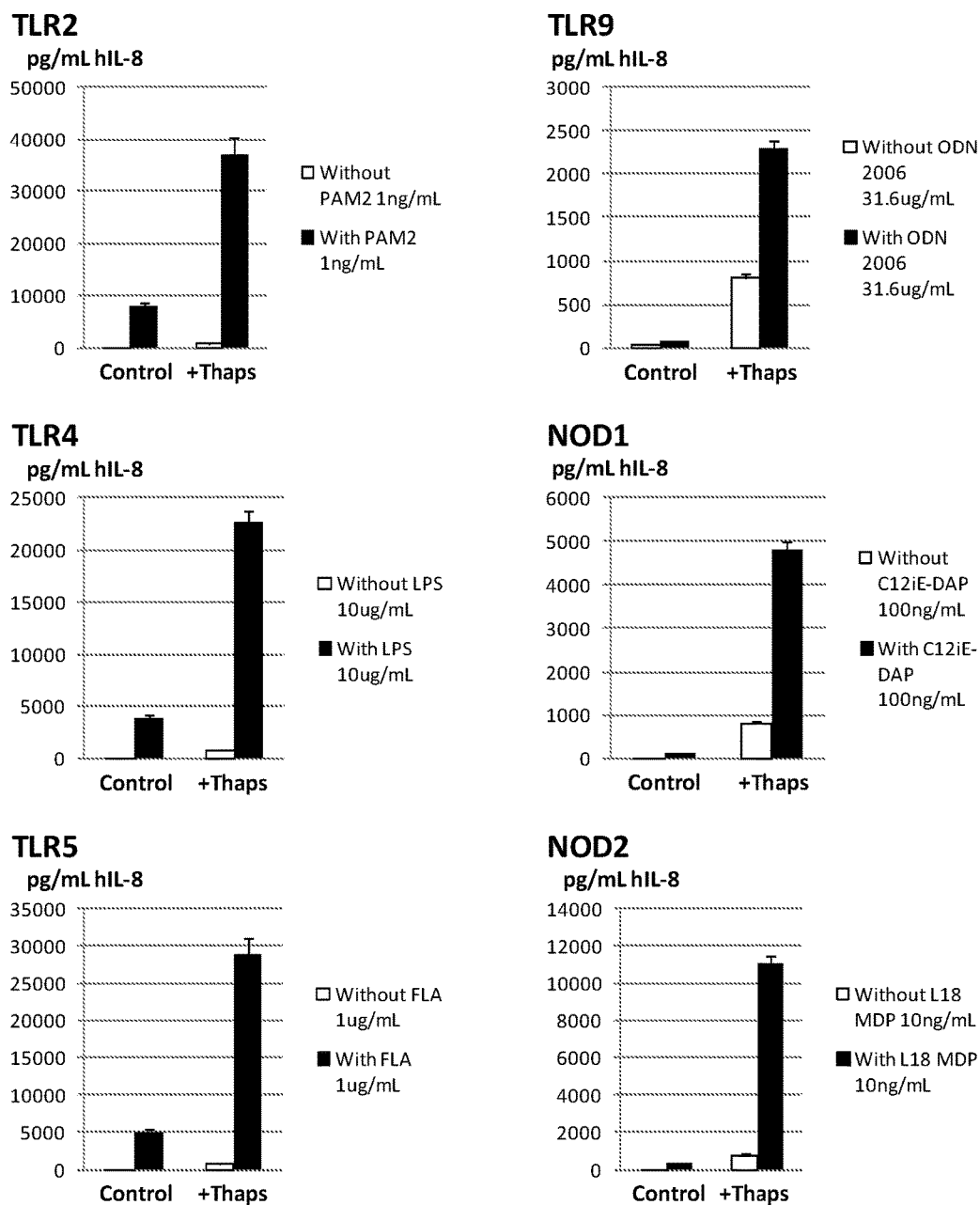

More specifically, FIG. 2A shows graphs depicting the synergistic effect of suboptimal doses of A23187 to augment cellular response for toll-like receptor (TLR) family members (TLR2, TLR4, TLR5, TLR9), and NOD family members (NOD1, NOD2). FIG. 2B shows graphs depicting the synergistic effect of suboptimal doses of ionomycin to augment cellular response for toll-like receptor (TLR) family members (TLR2, TLR4, TLR5, TLR9), and NOD family members (NOD1, NOD2). FIG. 2C shows graphs depicting the synergistic effect of suboptimal doses of cyclopiazonic acid to augment cellular response for toll-like receptor (TLR) family members (TLR2, TLR4, TLR5), and NOD family members (NOD1, NOD2). FIG. 2D shows graphs depicting the synergistic effect of suboptimal doses of 2,5-di(tert-butyl) hydroquinone (DBHQ) to augment cellular response for toll-like receptor (TLR) family members (TLR2, TLR4, TLR5), and NOD family members (NOD1, NOD2). FIG. 2E shows graphs depicting the synergistic effect of suboptimal doses of thapsigargin to augment cellular response for toll-like receptor (TLR) family members (TLR2, TLR4, TLR5, TLR9), and NOD family members (NOD1, NOD2). The doses used in this experiment were 20 nM for thapsigargin, 316 nM for A23187, 1 µM for ionomycin, 10 µM for cyclopiazonic acid, and 31.6 µM for DBHQ.

As can be readily appreciated, the synergistic effect with respect to IL-8 production was observed for all of the tested TLR and NOD family members and suitable ligands, while all of the tested calcium flux agonists were used at suboptimal concentration. Thus, a clear pattern of adjuvant activity of calcium flux agonists on the immune response, and especially on IL-8 production and NF-κB signaling is evident where the immune response is associated with a TLR- or NOD-mediated event.

Figure 3A:
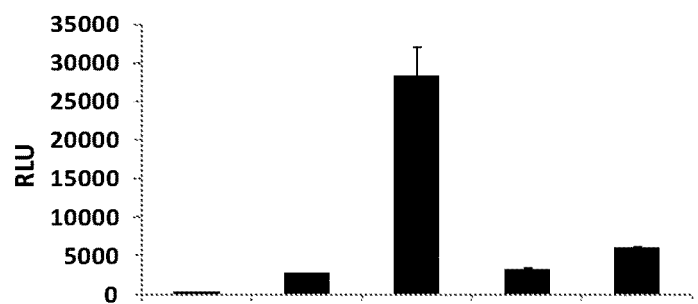
FIGS. 3A-3C show graphs depicting the extracellular requirement of $Ca^{2+}$ for calcium flux agonist signal amplification.
Figure 3B:
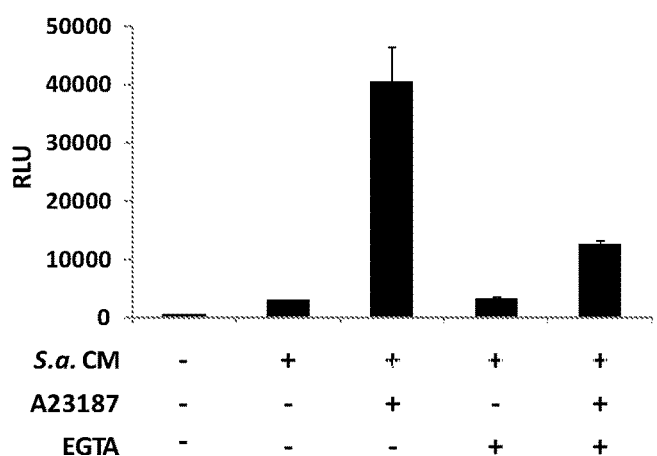
Figure 3C:
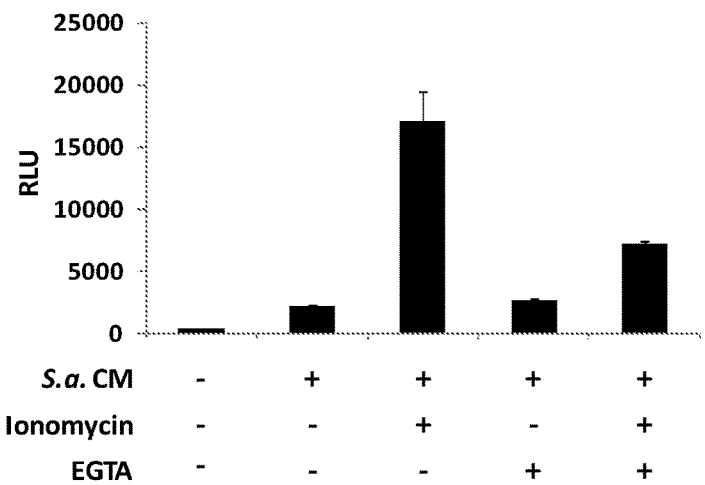

To determine whether the observed enhancement in activation of κB-LUC THP-1 cells by bacterial products achieved by suboptimal thapsigargin treatment was also true for the calcium ionophores A23187 and ionomycin, the experiment was repeated using these ionophores at the suboptimal doses of 316 nM and 1 µM, respectively. In all three cases, recognition of *S. aureus* conditioned/spent media was significantly enhanced in the presence of any of the calcium flux agonists (FIGS. 3A-3C). Perhaps of equal interest, the calcium flux-induced synergy could be inhibited by the addition of the extracellular chelator EGTA (1 mM) as can be readily seen from the Figures.

What is claimed is:

1. A method of improving healing of a sterile or toll-like receptor (TLR)/nucleotide-binding oligomerization domain receptor (NOD) ligand-poor wound, comprising:
    administering a $Ca^{2+}$-flux agonist (CFA) at a concentration and a pattern recognition receptor (PRR) ligand to a patient under a protocol that ensures presence of at least a portion of the CFA and at least a portion of the PRR ligand at the wound;
    wherein the concentration of CFA is below an amount providing the maximum response obtainable with the CFA in the absence of the PRR ligand;
    wherein the portion of the CFA and the portion of the PRR ligand are present in the wound in an amount effective to improve healing of the wound;
    wherein the PRR ligand is selected from the group consisting of Pam2CSK4, Pam2CYS, PAM2, ODN2006, lipopolysaccharide, C12iE-DAP, flagellin, and muramyl dipeptide; and
    wherein the CFA is selected from the group consisting of ionomycin, A23187, thapsigargin, cyclopiazonic acid, and 2,5-di-tert-butylhydroquinone (DBHQ).

2. The method of claim 1, wherein the CFA and PRR ligand are present in a single formulation that is formulated for topical administration.

3. The method of claim 1, wherein at least one of the CFA and PRR ligand are coupled to a surface of a medical item for wound treatment.

4. The method of claim 3, wherein the medical item for wound treatment is a suture, a staple, a clamp, an implant, or wound dressing.

5. The method of claim 1, wherein the wound is produced by a surgical procedure, or is a traumatic injury without an acute or persistent infection.

6. The method of claim 1, wherein the improved wound healing is characterized by at least one of reduced time to closure of a surface wound, reduced incidence of infection of the wound, and increased tissue remodeling within the wound.

7. The method of claim 1, wherein the protocol comprises directly and contemporaneously contacting the wound with the CFA and the PRR ligand.

8. The method of claim 7, wherein the step of contacting is topical administration to the wound and/or exposing the wound to a medical item for wound treatment to which the CFA and PRR are coupled.

9. The method of claim 1, wherein the CFA and the PRR ligand are present in synergistic quantities with respect to the improvement of the wound healing.

10. A method of treating a sterile or TLR/NOD ligand-poor wound, comprising:
    administering to the wound a pattern recognition receptor (PRR) ligand to produce at the wound site a non-saturating stimulus for a TLR and/or NOD signaling pathway;
    administering to the wound a $Ca^{2+}$-flux agonist (CFA) in an amount effective to amplify the stimulus;
    wherein amplification of the stimulus is performed under a protocol that improves healing of the wound;
    wherein the PRR ligand is selected from the group consisting of Pam2CSK4, Pam2CYS, PAM2, ODN2006, lipopolysaccharide, C12iE-DAP, flagellin, and muramyl dipeptide; and wherein the CFA is selected from the group consisting of ionomycin, A23187, thapsigargin, cyclopiazonic acid, and 2,5-di-tert-butylhydroquinone (DBHQ).

11. The method of claim 10, wherein the CFA and PRR ligand are topically administered to the wound.

12. The method of claim 10, wherein the CFA and PRR ligand are coupled to a surface of a medical item for wound treatment, and wherein the steps of administering are performed by contacting the wound with the medical item.

* * * * *